United States Patent
Kim et al.

(10) Patent No.: US 10,641,601 B2
(45) Date of Patent: May 5, 2020

(54) DUAL BEAM OPTICAL COHERENCE TOMOGRAPHY WITH SIMULTANEOUS ORTHOGONAL SCANNING

(71) Applicant: KOREA UNIVERSITY RESEARCH AND BUSINESS FOUNDATION, Seoul (KR)

(72) Inventors: Beop-Min Kim, Seoul (KR); Hyung-Jin Kim, Seoul (KR); Byeong-Joo Song, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 24 days.

(21) Appl. No.: 16/030,612

(22) Filed: Jul. 9, 2018

(65) Prior Publication Data

US 2019/0078872 A1    Mar. 14, 2019

(30) Foreign Application Priority Data

Sep. 8, 2017  (KR) .................... 10-2017-0115055
Jun. 7, 2018  (KR) .................... 10-2018-0065619

(51) Int. Cl.
*G01B 9/02* (2006.01)
*A61B 5/00* (2006.01)
*A61B 3/10* (2006.01)

(52) U.S. Cl.
CPC .......... *G01B 9/02091* (2013.01); *A61B 3/102* (2013.01); *A61B 5/0066* (2013.01); *G01B 9/02011* (2013.01); *G01B 9/02015* (2013.01); *G01B 9/02027* (2013.01); *G01B 2290/70* (2013.01)

(58) Field of Classification Search
CPC ............ G01B 9/02027; G01B 9/02091; G01B 2290/70; A61B 3/102; A61B 5/0066
See application file for complete search history.

(56) References Cited

U.S. PATENT DOCUMENTS

| | | | |
|---|---|---|---|
| 9,433,353 B2* | 9/2016 | Hanebuchi | A61B 3/102 |
| 2008/0002183 A1* | 1/2008 | Yatagai | G01N 21/4795 356/73 |
| 2016/0106319 A1* | 4/2016 | Yasuno | A61B 5/0066 600/425 |
| 2016/0313112 A1* | 10/2016 | Yamanari | A61B 3/102 |

(Continued)

FOREIGN PATENT DOCUMENTS

| | | |
|---|---|---|
| JP | 2014-228473 A | 12/2014 |
| JP | 2016-086867 A | 5/2016 |
| KR | 10-1287289 B1 | 7/2012 |

OTHER PUBLICATIONS

Baumann, Bernhard et al. "Swept source / Fourier domain polarization sensitive optical coherence tomography with a passive polarization delay unit". Optics Express, vol. 20, No. 9, Apr. 23, 2012, pp. 10218-10230. (Year: 2012).*

(Continued)

*Primary Examiner* — Michael A Lyons
(74) *Attorney, Agent, or Firm* — NSIP Law

(57) ABSTRACT

Disclosed herein is a simultaneous orthogonal scanning dual beam OCT system. The simultaneous orthogonal scanning dual beam OCT system includes: a light source 10; a light distribution unit 20; a sample arm 40; a reference arm 50; a interference unit 60; and a detection unit 70.

15 Claims, 8 Drawing Sheets

(56) References Cited

U.S. PATENT DOCUMENTS

2017/0031143 A1* 2/2017 Yao .................... G02B 21/0028
2018/0035894 A1* 2/2018 Yamanari ............. A61B 5/0066

OTHER PUBLICATIONS

Jeong, Hyun-Woo et al. "Spectral-domain OCT with dual illumination and interlaced detection for simultaneous anterior segment and retina imaging". Optics Express, vol. 20, No. 17, Aug. 13, 2012, pp. 19148-19159. (Year: 2012).*

Kim, Hyung-Jin et al. "High-resolution, dual-depth spectral-domain optical coherence tomography with interlaced detection for whole-eye imaging". Applied Optics, vol. 55, No. 26, Sep. 10, 2016, pp. 7212-7217. (Year: 2016).*

Yoon, Y., et al., "Dark-Field Polarization-Sensitive Optical Coherence Tomography", *Optical Society of America*, vol. 23 No. 10, May 2015, pp. 1-13 (13 pages in English).

Korean Notice of Allowance dated Jan. 6, 2020 in corresponding Korean Patent Application No. 10-2018-0065619 (2 pages in Korean).

* cited by examiner

DUAL BEAM OPTICAL COHERENCE TOMOGRAPHY WITH SIMULTANEOUS ORTHOGONAL SCANNING

CROSS-REFERENCE TO RELATED APPLICATIONS

This application claims the benefit under 35 USC 119(a) of Korean Patent Application Nos. 10-2017-0115055 filed on Sep. 8, 2017 and 10-2018-0065619 filed on Jun. 7, 2018 in the Korean Intellectual Property Office, the entire disclosure of which is incorporated herein by reference for all purposes.

FIELD OF THE INVENTION

The present invention relates to a simultaneous orthogonal scanning dual beam optical coherence tomography system, and more specifically to an optical coherence tomography system which can simultaneously acquire two images through scanning in perpendicular directions.

DESCRIPTION OF THE RELATED ART

Recently, optical coherence tomography (OCT) has attracted attention in the field of optical medical devices. An OCT system is a high-resolution imaging device that creates a visual representation of a microstructure inside living tissue through combination of optical interference and confocal microscopy. Such an OCT system can acquire a high-resolution sectional image of living tissue in a non-invasive manner and is thus used for clinical or therapeutic purposes in dermatology, ophthalmology, internal medicine, dentistry, etc. Particularly, in ophthalmology, the OCT system is mainly used for angiography. In the case of retinal diseases, it is possible to diagnose the diseases and analyze progression of the diseases through the distribution or shape of blood vessels. When the same region of the retina is scanned by the OCT system, layered structures or solid tissues of the retina exhibit a low degree of decorrelation between scanning images, whereas blood vessels exhibit a high degree of decorrelation between scanning images due to scatterers such as fluids and hemocytes flowing in the blood vessels, thereby allowing acquisition of a vascular image.

Angiography with the OCT system is highly sensitive to eye motion since it is based on the degree of decorrelation between images of the same region of the retina. Eye motion is due to various factors such as heartbeat, respiration or focus shift and causes distortion of an image (see (a) of FIG. 1) or creates noise in a vascular image (see (b) of FIG. 1).

A conventional OCT system acquires a 2D image (XZ plane image) by scanning a subject with a point-focused beam. Here, the scanning direction (X-axis direction) is referred to as a fast axis and a direction perpendicular thereto (Y-axis direction), that is, a direction in which 2D images are stacked while moving the scan beam point-by-point for acquisition of a 3D image, is referred to as a slow axis. Here, the terms "fast axis" and "slow axis" indicate that there is a time gap between scanning processes. In vascular imaging that visualizes a degree of decorrelation between images, the effect of eye motion mainly appears on the slow axis due to the time gap.

In order to compensate for the effects of eye motion, there has been proposed a method of performing an additional scanning process in the slow axis direction or a method of acquiring and optimizing several 3D images. However, these methods have a problem in that the speed of acquisition of a vascular image is slowed down due to necessity of additional scanning or repeated scanning of the same region.

Therefore, there is a need for a solution to overcome such drawbacks of conventional OCT systems.

SUMMARY OF THE INVENTION

The present invention has been made in an effort to solve the problems of the prior art and intends to provide a simultaneous orthogonal scanning dual beam OCT system which can acquire different images perpendicular to one another through a single scanning process by allowing a subject to be irradiated with a horizontally polarized beam and a vertically polarized beam perpendicular to one another at the same time.

The present invention also intends to provide a simultaneous orthogonal scanning dual beam OCT system which is not affected by focal distance while preventing reduction in scanning range using a 4f system in a sample arm that emits light to a subject and receives reflected light from the subject.

The present invention also intends to provide a simultaneous orthogonal scanning dual beam OCT system which can correct images through detection of motion of a subject during scanning.

A simultaneous orthogonal scanning dual beam optical coherence tomography (OCT) system according to one aspect of the present invention includes: a light source generating broadband light; a light distribution unit distributing the light from the light source; a sample arm splitting a fraction of the light from the light distribution unit into a horizontally polarized beam and a vertically polarized beam traveling along different optical paths, simultaneously emitting the horizontally polarized beam and the vertically polarized beam to a subject after converting the horizontally polarized beam and the vertically polarized beam such that scanning directions thereof are perpendicular to one another, and receiving a reflected horizontally polarized beam and a reflected vertically polarized beam from the subject; a reference arm splitting the other fraction of the light from the light distribution unit and generating a reference beam containing a horizontal polarization component and a vertical polarization component; an interference unit receiving the reflected horizontally polarized beam, the reflected vertically polarized beam, and the reference beam and generating an interference signal of horizontal polarization components and an interference signal of vertical polarization components allowing simultaneous acquisition of an XZ plane image and a YZ plane image perpendicular to one another; and a detection unit converting the interference signals into electrical signals.

The simultaneous orthogonal scanning dual beam OCT system may further include a polarized beam distribution unit splitting a fraction of the light from the light distribution unit into a horizontally polarized beam and a vertically polarized beam and emitting the horizontally polarized beam and the vertically polarized beam to the sample arm.

The polarized beam distribution unit may include: a polarization beam splitter splitting light from the light distribution unit into a first horizontally polarized beam and a first vertically polarized beam and emitting the first horizontally polarized beam and the first vertically polarized beam; a first reflective mirror disposed on a first optical path along which the emitted first vertically polarized beam travels; a first quarter-wave plate disposed between the polarization beam splitter and the first reflective mirror to convert the first vertically polarized beam into a second horizontally polarized beam and emit the second horizontally polarized beam to the polarization beam splitter; a second reflective mirror disposed on a second optical path along which the emitted first horizontally polarized beam travels; and a second quarter-wave plate disposed between the polarization beam splitter and the second reflection mirror to convert the first horizontally polarized beam into a second vertically polarized beam and emit the second vertically polarized beam to the polarization beam splitter, wherein the polarization beam splitter emits the second horizontally polarized beam and the second vertically polarized beam to the sample arm and receives and transmits the reflected horizontally polarized beam and the reflected vertically polarized beam.

In the polarized beam distribution unit, the first reflective mirror may be moved along the first optical path or the second reflective mirror may be moved along the second optical path such that the second horizontally polarized beam has a different optical length than the second vertically polarized beam.

The reference arm may include a linear polarizer generating the reference beam by converting light from the light distribution unit into a 45-degree polarized beam.

The interference unit may include one interferometer generating the interference signals by allowing the reflected horizontally polarized beam and the reflected vertically polarized beam to interfere with the reference beam.

The light distribution unit may include: a primary beam splitter splitting light generated by the light source into a first distributed beam and a second distributed beam; a first beam splitter transmitting a fraction of the first distributed beam to the polarized beam distribution unit and transmitting the other fraction of the first distributed beam to the reference arm; and a second beam splitter transmitting a fraction of the second distributed beam to the polarized beam distribution unit and transmitting the other fraction of the second distributed beam to the reference arm.

The polarized beam distribution unit may include a polarization beam splitter splitting a fraction of the first distributed beam into a first horizontally polarized beam and a first vertically polarized beam and emitting the first horizontally polarized beam to the sample arm, receiving the reflected horizontally polarized beam and transmitting the reflected horizontally polarized beam to the first beam splitter, splitting a fraction of the second distributed beam into a second horizontally polarized beam and a second vertically polarized beam and emitting the second vertically polarized beam to the sample arm, and receiving the reflected vertically polarized beam and transmitting the reflected vertically polarized beam to the second beam splitter.

The reference arm may include: a first reference arm polarization beam splitter splitting the other fraction of the first distributed beam into a third horizontally polarized beam and a third vertically polarized beam, transmitting the third horizontally polarized beam, splitting the other fraction of the second distributed beam into a fourth horizontally polarized beam and a fourth vertically polarized beam, and transmitting the fourth vertically polarized beam; and a second reference arm polarization beam splitter receiving and separately transmitting the third horizontally polarized beam and the fourth vertically polarized beam.

The interference unit may include: a first interferometer receiving the reflected horizontally polarized beam and the third horizontally polarized beam from the first beam splitter and the second reference arm polarization beam splitter, respectively and generating the interference signal of horizontal polarization components; and a second interferometer receiving the reflected vertically polarized beam and the fourth vertically polarized beam from the second beam splitter and the second reference arm polarization beam splitter, respectively, and generating the interference signal of vertical polarization components.

The detection unit may include: a first balanced photodetector converting the interference signal of horizontal polarization components into an electrical signal; and a second balanced photodetector converting the interference signal of vertical polarization components into an electrical signal.

The reference arm may include: a polarization beam splitter splitting light from the light distribution unit into a first horizontally polarized beam and a first vertically polarized beam and emitting the first horizontally polarized beam and the first vertically polarized beam; a first reflective mirror disposed on a first optical path along which the emitted first vertically polarized beam travels; a first quarter-wave plate disposed between the polarization beam splitter and the first reflective mirror to convert the first vertically polarized beam into a second horizontally polarized beam and emit the second horizontally polarized beam to the polarization beam splitter; a second reflective mirror disposed on a second optical path along which the first horizontally polarized beam travels; and a second quarter-wave plate disposed between the polarization beam splitter and the second reflective mirror to convert the first horizontally polarized beam into a second vertically polarized beam and emit the second vertically polarized beam to the polarization beam splitter, wherein the polarization beam splitter emits the second horizontally polarized beam and the second vertically polarized beam to the interference unit.

The sample arm may include: a galvanometer scanner including a pair of scanning mirrors rotating about rotational axes located in X-axis and Z-axis directions, respectively in a virtual XYZ three-dimensional space (the X-axis, Y-axis, and Z-axis directions being perpendicular to one another), the galvanometer scanner sending the received light in the Z-axis direction; a first sample arm polarization beam splitting the light from the galvanometer scanner into a fifth horizontally polarized beam and a fifth vertically polarized beam and emitting the fifth horizontally polarized beam and the fifth vertically polarized beam in the Z-axis and X-axis directions, respectively; a first mirror unit including a $1\text{-}1^{st}$ mirror reflecting the fifth horizontally polarized beam in the Y-axis direction, a $1\text{-}2^{nd}$ mirror reflecting the fifth horizontally polarized beam from the $1\text{-}1^{st}$ mirror in the Z-axis direction, and a $1\text{-}3^{rd}$ mirror reflecting the fifth horizontally polarized beam from the $1\text{-}2^{nd}$ mirror in the X-axis direction; a half-wave plate converting the fifth horizontally polarized beam from the $1\text{-}3^{rd}$ mirror into a sixth vertically polarized beam and emitting the sixth vertically polarized beam; a second mirror unit including a $2\text{-}1^{st}$ mirror reflecting the emitted fifth vertically polarized beam in the Y-axis direction and a $2\text{-}2^{nd}$ mirror reflecting the fifth vertically polarized beam from the $2\text{-}1^{st}$ mirror in the Z-axis direction, the second mirror unit converting the fifth vertically polarized beam into a sixth horizontally polarized beam; and a second sample arm polarization beam splitter receiving the sixth horizontally polarized beam and the sixth vertically polarized beam and simultaneously emitting the sixth horizontally polarized beam and the sixth vertically polarized beam in the Z-axis direction, such that the sample arm sends the sixth horizontally polarized beam, a scanning direction of which is the Y-axis direction, and the sixth vertically polarized beam, a scanning direction of which is the X-axis direction, to the subject.

The sample arm may further include a 4f system including a pair of lenses and disposed on at least one of an optical path between the pair of scanning mirrors, an optical path passing through the second sample arm polarization beam splitter, and an optical path between the first sample arm polarization beam splitter and the half-wave plate.

The simultaneous orthogonal scanning dual beam OCT system may further include an image correction unit measuring a correlation between the images acquired during scanning, detecting motion of the subject, and correcting the images.

Features and advantages of the present invention will become apparent from the detailed description of the following embodiments in conjunction with the accompanying drawings.

Before describing the present invention, it should be understood that the terms and words used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation for the invention.

The simultaneous orthogonal scanning dual beam OCT system of the present invention acquires different images perpendicular to one another through a single scanning process and thus can obtain a noise-free 3D image of a subject at high speed.

In addition, the simultaneous orthogonal scanning dual beam OCT system of the present invention uses a 4f system in a sample arm and thus can be unaffected by the focal distance of a lens while preventing reduction in scanning range despite having many optical components disposed therein.

Furthermore, the simultaneous orthogonal scanning dual beam OCT system of the present invention can detect motion of a subject during scanning and compensate for the motion, thereby acquiring an accurate 3D image.

DETAILED DESCRIPTION OF THE INVENTION

Figure 1A:
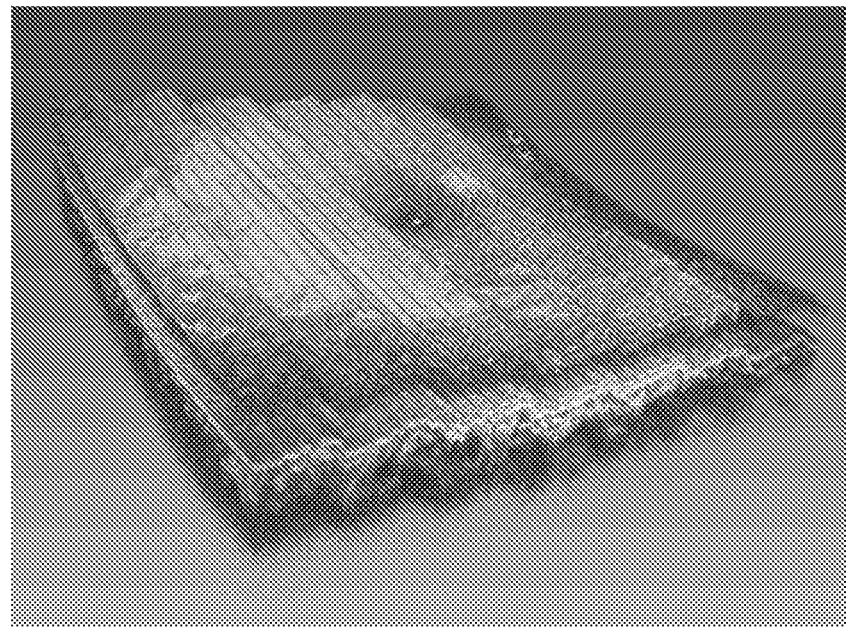
FIG. 1 shows images acquired by a conventional OCT system.

The above and other aspects, features, and advantages of the present invention will become apparent from the detailed description of the following embodiments in conjunction with the accompanying drawings. Like components will be denoted by like reference numerals throughout the specification. It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Description of known functions and constructions which may unnecessarily obscure the subject matter of the present invention will be omitted.

Hereinafter, embodiments of the present invention will be described with reference to the accompanying drawings.

Figure 2:
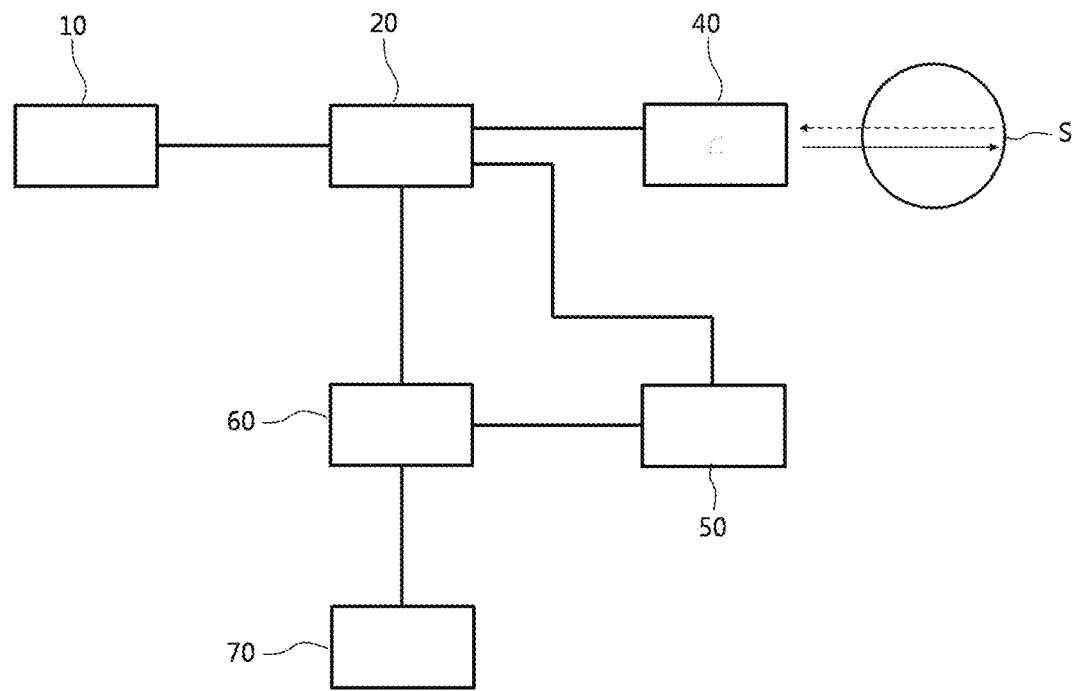
FIG. 2 is a block diagram of a simultaneous orthogonal scanning dual beam OCT system according to a first embodiment of the present invention.

FIG. 2 is a block diagram of a simultaneous orthogonal scanning dual beam optical coherence tomography (OCT) system according to a first embodiment of the present invention.

Referring to FIG. 2, a simultaneous orthogonal scanning dual beam OCT system according to this embodiment includes: a light source 10 generating broadband light; a light distribution unit 20 distributing the light from the light source 10; a sample arm 40 splitting a fraction of the light from the light distribution unit 20 into a horizontally polarized beam and a vertically polarized beam traveling along different optical paths, simultaneously emitting the horizontally polarized beam and the vertically polarized beam to a subject S after converting the horizontally polarized beam and the vertically polarized beam such that scanning directions thereof are perpendicular to one another, and receiving a reflected horizontally polarized beam and a reflected vertically polarized beam from the subject S; a reference arm 50 splitting the other fraction of the light from the light distribution unit 20 and generating a reference beam containing a horizontal polarization component and a vertical polarization component; an interference unit 60 receiving the reflected horizontally polarized beam, the reflected vertically polarized beam, and the reference light and generating an interference signal of horizontal polarization components and an interference signal of vertical polarization components allowing simultaneous acquisition of an XZ plane image and a YZ plane image perpendicular to one another; and a detection unit 70 converting the interference signals into electrical signals.

The present invention is directed to an OCT system and has been made in an effort to solve the problem that, in acquisition of vascular images through angiography using a conventional OCT system in ophthalmology, image distortion or noise occurs due to eye motion and an additional scanning process is thus required to compensate for the effect of eye motion, making image acquisition time-consuming.

Such a conventional OCT system scans a subject in the X-axis direction with a point-focused beam to acquire a 2D image (2D XZ plane image) and repeats the same process while moving the scan beam point-by-point in the Y-axis direction to acquire other 2D images (2D XZ plane images), followed by stacking of the acquired 2D images. Here, the scanning direction (X-axis direction) is referred to as a "fast axis", and the perpendicular direction (Y-axis direction) with respect thereto is referred to as a "slow axis". The X-axis and the Y-axis are perpendicular to each other, and, when the depth direction of the subject is defined as the Z-axis, the X-axis and the Y-axis refer to two axes perpendicular to the Z-axis, respectively (the same shall apply hereinafter). After X-fast scan is completed, Y-fast scan in which the OCT system scans the subject in the Y-axis direction (fast axis) while moving the beam point-by-point in the X-axis (slow axis) direction is additionally performed in the same manner as above, thereby acquiring a three-dimensional image. In this case, it takes a long time to acquire an image due to the additional Y-fast scan process, and the acquired image is affected by eye motion due to a time gap between X-fast scan and Y-fast scan, such that an additional scan process is required to correct the image, or acquisition and optimization of several 3D images are required.

Embodiments of the present invention provide an OCT system which uses two light beams having perpendicular scanning directions such that one beam scans a subject in the X-axis (fast axis) direction (i.e., performs X-fast scan) at the same time as the other beam scans the subject in the Y-axis (fast axis) direction (i.e., performs Y-fast scan), thereby simultaneously acquiring a 2D XZ plane image and a 2D YZ plane image.

Since a dual-beam OCT system for simultaneous orthogonal scanning according to the present invention may be applied not only to ophthalmology, but also to other medical fields such as dermatology, internal medicine, and dentistry, the term "subject S" may refer to various microstructures in the human tissue to be imaged, despite referring to the retina herein.

As described above, the simultaneous orthogonal scanning dual beam OCT system of the present invention includes the light source 10, the light distribution unit 20, the sample arm 40, the reference arm 50, the interference unit 60, and the detection unit 70.

The light source 10 includes a coherent light source to generate broadband light. The generated broadband light is transmitted to the light distribution unit 20. Here, the light travels along a transmission line, wherein the transmission line may be implemented with an optical fiber. Other transmission lines connected between the aforementioned components, described below, may also be implemented with optical fibers.

The light distribution unit 20 splits light from the light source unit 10 into multiple beams. The light distribution unit 20 may include at least one beam splitter, wherein the beam splitter may be implemented with a fiber coupler and the number thereof will be described in detail in embodiments set forth below. In this embodiment, a fraction of the light from the light distribution unit 20 is transmitted to the sample arm 40 and the other fraction of the light is transmitted to the reference arm 50. In another embodiment set forth below, the fraction of light from the light distribution unit 20 is transmitted to the sample arm 40 via a polarized beam distribution unit 30.

In this embodiment, the sample arm 40 splits a fraction of the light from the light distribution unit 20 into a horizontally polarized beam and a vertically polarized beam. Here, the horizontally polarized beam and the vertically polarized beam travel along different optical paths and are emitted to the subject S after being converted such that scanning directions thereof are perpendicular to one another. The emitted horizontally polarized beam and vertically polarized beam are reflected by the subject (S) and return to the sample arm 40. Hereinafter, the horizontally polarized beam reflected by the subject S will be referred to as a "reflected horizontally polarized beam" and the vertically polarized beam reflected by the subject S will be referred to as a "reflected vertically polarized beam".

The reflected horizontally polarized beam and the reflected vertically polarized beam are transmitted back to the light distribution unit 20 via the sample arm 40 and eventually transmitted to the interference unit 60 described below.

The initial horizontally polarized beam and vertically polarized beam are converted into a vertically polarized beam and a horizontally polarized beam having perpendicular scanning directions, respectively, by components of the sample arm 40 described below before simultaneously striking the subject S. Details thereof will be described below with reference to FIGS. 7 and 8.

The reference arm 50 splits a fraction of the light from the light distribution unit 20 to generate a reference beam containing a horizontal polarization component and a vertical polarization component. The generated reference beam is transmitted to the interference unit 60.

The interference unit 60 receives the reflected horizontally polarized beam and the reflected vertically polarized beam from the light distribution unit 20 and receives the reference beam from the reference arm 50 to generate an interference signal. Here, the interference unit 60 includes at least one interferometer, wherein the interferometer may be implemented with a fiber coupler. The number of interferometers will be described in detail in embodiments set forth below.

Here, the interference signal includes two interference signals generated by interference between the reflected horizontally polarized beam and the horizontal polarization component of the reference beam and interference between the reflected vertically polarized beam and the vertical polarization component of the reference beam, respectively. Herein, the former is referred to as an "interference signal of horizontal polarization components" and the latter is referred to as an "interference signal of vertical polarization components". An image of a predetermined region of the subject S may be acquired through the two interference signals.

Since the horizontally polarized beam and vertically polarized beam having perpendicular scanning directions strike the subject S at the same time such that one beam scans a predetermined region of the subject S along the X-axis (fast axis) at the same time as the other beam scans the same predetermined region along the Y-axis (fast axis), an XZ plane image and a YZ plane image perpendicular to one another can be acquired at the same time.

Thus, in acquisition of an image of the retina, unlike a conventional OCT system, the OCT system of the present invention can scan the retina in the perpendicular directions at the same time, whereby a high-quality vascular image unaffected by eye motion can be obtained through post-processing of an acquired ocular image. Further, unlike a conventional OCT system which requires a time-consuming additional scan process to compensate for eye motion, the OCT system of the present invention does not require any additional scan process, thereby reducing the time for image acquisition. Moreover, even when several 3D images are taken and averaged to improve quality of a vascular image, the OCT system of the present invention can shorten the imaging time, thereby minimizing both patient discomfort and influence of eye motion during the imaging process.

In order to acquire two perpendicular images, it is necessary to convert the interference signals into electrical signals. Here, conversion of the interference signals into electrical signals is performed by the detection unit 70. The detection unit 70 may include a balanced photodetector (BPD) to detect the interference signals.

As described above, in the simultaneous orthogonal scanning dual beam OCT system of the present invention, the horizontally polarized beam and the vertically polarized beam having struck the subject S at the same time and returned therefrom cause interference with the reference beam having passed through the reference arm 50, such that two perpendicular images can be acquired. Now, details thereof will be described in the following embodiments.

Figure 3:
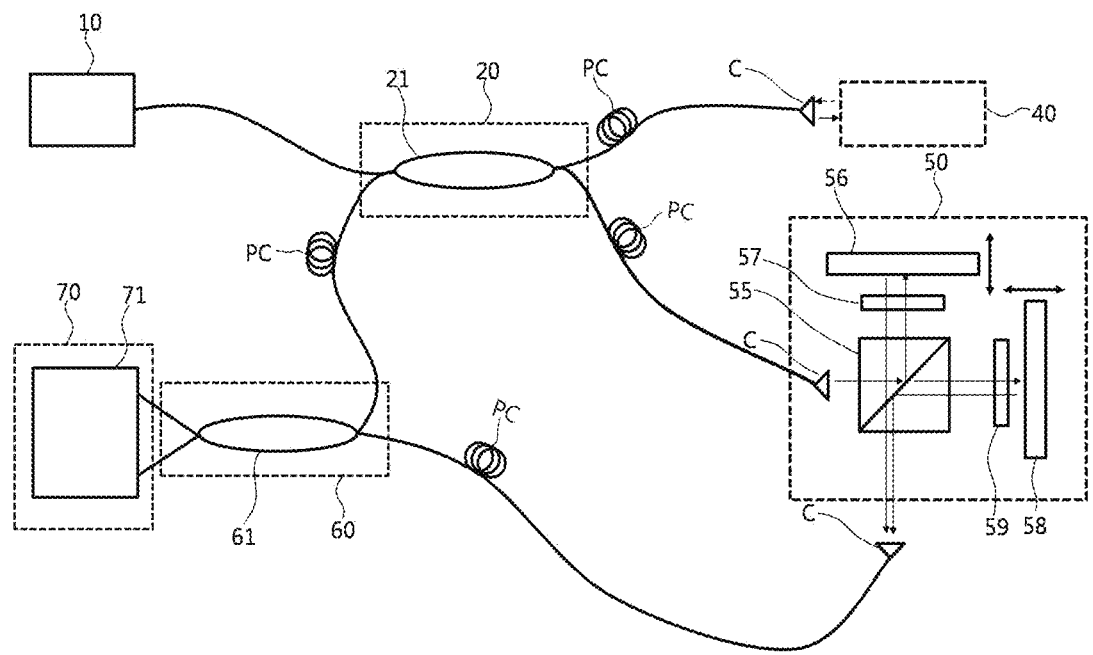
FIG. 3 is a block diagram of a simultaneous orthogonal scanning dual beam OCT system according to a 1-1$^{st}$ embodiment of the present invention.

FIG. 3 is a block diagram of a simultaneous orthogonal scanning dual beam OCT system according to a 1-$1^{st}$ embodiment of the present invention.

Referring to FIG. 3, a light distribution unit 20 of the simultaneous orthogonal scanning dual beam OCT system according to the 1-$1^{st}$ embodiment includes one fiber coupler 21 and transmits a fraction of light from a light source 10 and the other fraction to a sample arm 40 and a reference arm 50, respectively. In addition, the light distribution unit 20 receives a reflected horizontally polarized beam and vertically polarized beam returned via the sample arm 40 and transmits the reflected horizontally polarized beam and vertically polarized beam to an interference unit 60. In FIG. 3, the light incident on the sample arm 40 is represented by the solid line and the reflected horizontally polarized beam and the reflected vertically polarized beam are represented by the dotted line.

Here, transmission lines may be connected between the light source 10 and the light distribution unit 20, between the light distribution unit 20 and the sample arm 40, between the light distribution unit 20 and the reference arm 50, between the light distribution unit 20 and the interference unit 60, and between the reference arm 50 and the interference unit 60, respectively. Each of the transmission lines may be implemented with an optical fiber. In addition, a polarization controller (PC) may be disposed on at least one of the transmission lines excluding a transmission line between the light source 10 and the light distribution unit 20. Here, the polarization controller allows a light beam to have a quasi-Gaussian profile while maximizing intensity of the light beam.

The reference arm 50 may include a polarization beam splitter 55, a first reflective mirror 56, a first quarter-wave plate 57, a second reflective mirror 58, and a second quarter-wave plate 59.

The polarization beam splitter 55 splits light from the light distribution unit 20 into a first horizontally polarized beam and a first vertically polarized beam and emits the first horizontally polarized beam and the first vertically polarized beam. Referring to FIG. 3, the polarization beam splitter 55 allows a horizontal polarization component to pass in a straight light therethrough while allowing a vertical polarization component to be reflected 90 degrees thereby. Here, the solid lines represent incident light from the light distribution unit 20 and the horizontal and vertical polarization components of the incident light, respectively.

On a first optical path along which the emitted first vertically polarized beam travels, the first quarter-wave plate 57 and the first reflective mirror 56 are sequentially disposed in the traveling direction. Accordingly, the first vertically polarized beam is reflected by the first reflective mirror 56 to be returned to the polarization beam splitter 55. Here, since the first vertically polarized beam passes through the first quarter-wave plate 57 twice, the polarization direction of the first vertically polarized beam is changed 90 degrees, such that the first vertically polarized beam is converted into a second horizontally polarized beam, which passes in a straight line through the polarization beam splitter 55. In addition, the second quarter wave plate 59 and the second reflective mirror 58 are sequentially disposed on a second optical path along which the first horizontally polarized beam travels, such that the emitted first horizontally polarized beam is converted into a second vertically polarized beam in the process of being returned to the polarization beam splitter 55. The second horizontally polarized beam and the second vertically polarized beam are transmitted to the interference unit 60.

In the reference arm 50, the first reflective mirror 56 or the second reflective mirror 58 may be configured to be movable back and forth along a corresponding optical path, thereby adjusting optical length of each of the second horizontally polarized beam and the second vertically polarized beam. When the second horizontally polarized beam has a different optical length than the second vertically polarized beam, it is possible to prevent the two images from overlapping one another. In this way, the two images can be acquired using only one balanced photodetector 71.

Thus, the use of the reference arm 50 according to the present embodiment allows the detection unit 70 to be simply implemented with only one balanced photodetector 71.

The reference arm 50 may further include a collimator C. The collimator C may be disposed at an end of a transmission line from the light distribution unit 20 to the polarization beam splitter 55 and at an end of a transmission line from the polarization beam splitter 55 to the interference unit 60 where light exits the polarization beam splitter 55 to convert light entering/exiting the polarization beam splitter 55 into a parallel beam. In addition, the collimator may be further disposed at an end of a transmission line from the light distribution unit 20 to the sample arm 40 where light enters the sample arm 40.

In this embodiment, the interference unit 60 may include one interferometer 61. As described above, the interferometer 61 may be implemented with a fiber coupler, and one interferometer 61 may include one fiber coupler. The interferometer 61 is connected to the light distribution unit 20 and the reference arm 50. Thus, the interferometer 61 receives the reflected horizontally polarized beam and the reflected vertically polarized beam from the light distribution unit 20 while receiving the second horizontally polarized beam and the second vertically polarized beam from the reference arm 50 and generates an interference signal of horizontal polarization components through interference between the reflected horizontally polarized beam and the horizontal polarization component of the reference light while generating an interference signal of vertical polarization components through interference between the reflected vertically polarized beam and the vertical polarization component of the reference light. As described above, the two interference signals are transmitted to one balanced photodetector 71 to be converted into electrical signals.

Figure 4:
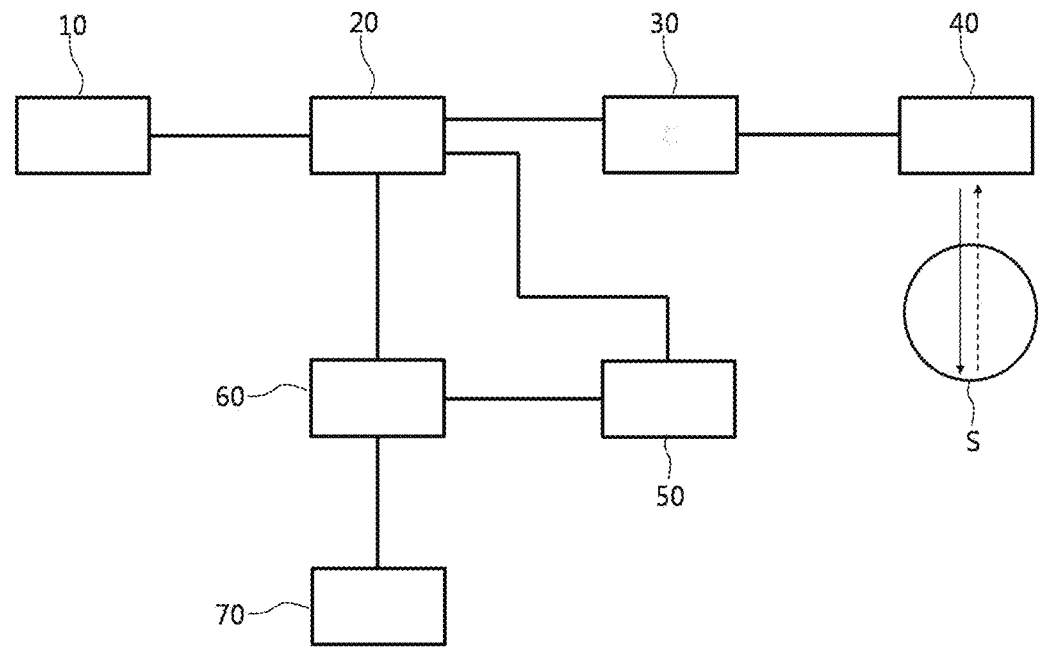
FIG. 4 is a block diagram of a simultaneous orthogonal scanning dual beam OCT system according to a second embodiment of the present invention.

FIG. 4 is a block diagram of a simultaneous orthogonal scanning dual beam OCT system according to a second embodiment of the present invention. The following description will focus on different features of the second embodiment from the first embodiment.

Referring to FIG. 4, the simultaneous orthogonal scanning dual beam OCT system according to this embodiment may further include a polarized beam distribution unit 30.

The polarized beam distribution unit 30 splits light from the light distribution unit 20 into a horizontally polarized beam and a vertically polarized beam. The polarized beam distribution unit 30 includes a polarization beam splitter (PBS) to split the incident light into the horizontally polarized beam and the vertically polarized beam and emit the horizontally polarized beam and the vertically polarized beam to a sample arm 40.

Here, the sample arm 40 receives the horizontally polarized beam and the vertically polarized beam from the polarized beam distribution unit 30 and emits the horizontally polarized beam and the vertically polarized beam to a subject S. Here, the emitted horizontally polarized beam and vertically polarized beam are reflected by the subject S and returned to the sample arm 40 (hereinafter, a "reflected horizontally polarized beam" and a "reflected vertically polarized beam").

The reference arm 50 converts a fraction of light from the light distribution unit 20 into a predetermined polarized beam. Here, the predetermined polarized beam contains a horizontal polarization component and a vertical polarization component and is transmitted to an interference unit 60.

The interference unit 60 receives the reflected horizontally polarized beam and the reflected vertically polarized beam from the polarized beam distribution unit 30 and receives the predetermined polarized beam from the reference arm 50 to generate an interference signal. The interference unit 60 may include at least one interferometer, wherein the interferometer may be implemented with a fiber coupler. The interference signal includes an interference signal of horizontal polarization components, generated by interference between the reflected horizontally polarized beam and the horizontal polarization component of the predetermined polarized beam and an interference signal of vertical polarization components, generated by interference between the reflected vertically polarized beam and the vertical polarization component of the predetermined polarized beam.

A detection unit 70 includes a balanced photodetector (BPD) to detect the interference signals.

Figure 5:
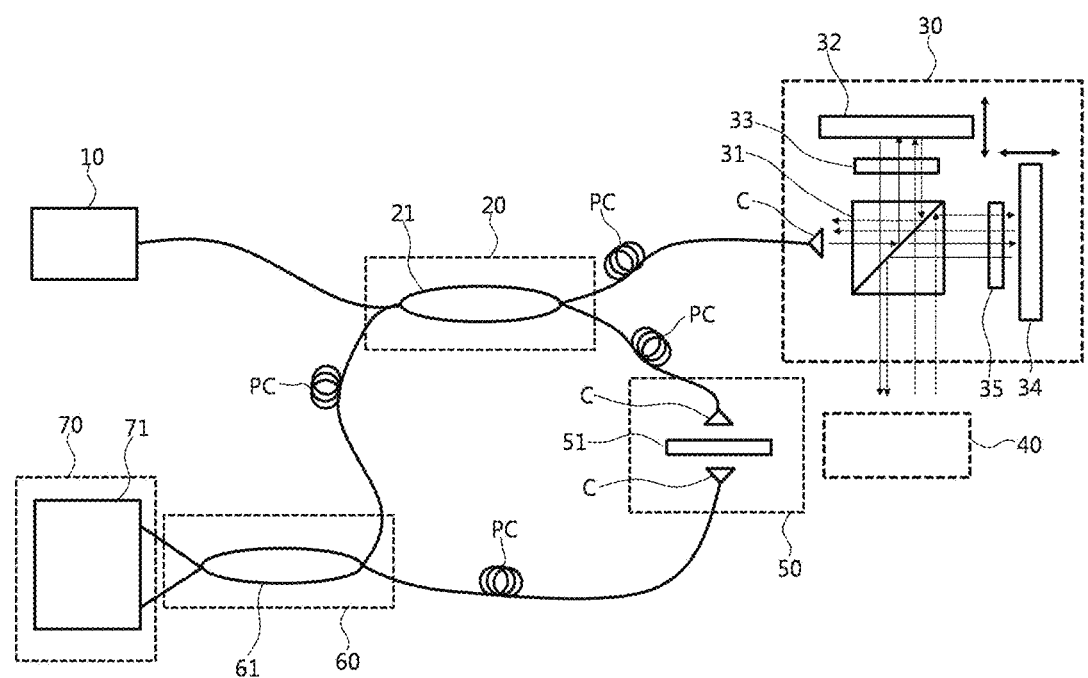
FIG. 5 is a block diagram of a simultaneous orthogonal scanning dual beam OCT system according to a 2-1$^{st}$ embodiment of the present invention.

FIG. 5 is a block diagram of a simultaneous orthogonal scanning dual beam OCT system according to a 2-1$^{st}$ embodiment of the present invention.

Referring to FIG. 5, a light distribution unit 20 of the simultaneous orthogonal scanning dual beam OCT system according to the 2-1$^{st}$ embodiment includes one fiber coupler 21 to transmit a fraction of light from a light source 10 to a polarized beam distribution unit 30 and the other fraction to a reference arm 50. In addition, the light distribution unit 20 receives a reflected horizontally polarized beam and a reflected vertically polarized beam returned through a sample arm 40 and the polarized beam distribution unit 30 and transmits the reflected horizontally polarized beam and the reflected vertically polarized beam to an interference unit 60.

Here, transmission lines may be connected between the light source 10 and the light distribution unit 20, between the light distribution unit 20 and the polarized beam distribution unit 30, between the light distribution unit 20 and the reference arm 50, between the light distribution unit 20 and the interference unit 60, and between the reference arm 50 and the interference unit 60, respectively. Each of the transmission lines may be implemented with an optical fiber. Further, a polarization controller (PC) may be disposed on at least one of the transmission lines excluding a transmission line between the light source 10 and the light distribution unit 20.

In this embodiment, the polarized beam distribution unit 30 splits light from the light distribution unit 20 into a first horizontally polarized beam and a first vertically polarized beam, converts the first horizontally polarized beam and the first vertically polarized beam into a second vertically polarized beam and a second horizontally polarized beam, respectively, emits the second vertically polarized beam and the second horizontally polarized beam to the sample arm 40, and transmits a reflected horizontally polarized beam and a reflected vertically polarized beam to the light distribution unit 20. Here, the reflected horizontally polarized beam and the reflected vertically polarized beam refer to the second horizontally polarized beam and the second vertically polarized beam reflected from a subject S, respectively.

Specifically, the polarized beam distribution unit 30 may include a polarization beam splitter 31, a first reflective mirror 32, a first quarter-wave plate 33, a second reflective mirror 34, and a second quarter-wave plate 35.

The polarization beam splitter 31 splits light from the light distribution unit 20 into a first horizontally polarized beam and a first vertically polarized beam and emits the first horizontally polarized beam and the first vertically polarized beam. Referring to FIG. 5, the polarization beam splitter 31 allows a horizontal polarization component to pass in a straight line therethrough while allowing a vertical polarization component to be reflected 90 degrees thereby. Here, the solid lines represent incident light from the light distribution unit 20 and horizontal and vertical polarization components of the incident light, respectively, and the dotted lines represent horizontal and vertical polarization components having been reflected from the subject S and entering the polarization beam splitter via the sample arm 40. Polarization beam splitters 36, 56, 57, 42, 46 shown in FIG. 6 to FIG. 8 also allow a horizontally polarized beam to pass in a straight line therethrough while allowing a vertically polarized beam to be reflected 90 degrees thereby.

On a first optical path along which the emitted first vertically polarized beam travels, the first quarter-wave plate 33 and the first reflective mirror 32 are sequentially disposed in the traveling direction. Accordingly, the emitted first vertically polarized beam is reflected by the first reflective mirror 32 and returned to the polarization beam splitter 31. Here, the first vertically polarized beam passes through the first quarter-wave plate 33 twice to be converted into a second horizontally polarized beam.

The second quarter-wave plate 35 and the second reflective mirror 34 are sequentially disposed on a second optical path along which the first horizontally polarized beam travels, such that the emitted first horizontally polarized beam is converted into a second vertically polarized beam in the process of being returned to the polarization beam splitter 31. The second horizontally polarized beam and the second vertically polarized beam are transmitted to the sample arm 40 via the polarization beam splitter 31. In addition, the reflected vertically polarized beam and reflected horizontally polarized beam returned from the subject S via the sample arm 40 are transmitted to the light distribution unit 20 via the polarized beam distribution unit 30.

In the polarized beam distribution unit 30, the first reflective mirror 32 or the second reflective mirror 34 may be configured to be movable back and forth along a corresponding optical path, thereby adjusting optical length of each of the second horizontally polarized beam and the second vertically polarized beam. When the second horizontally polarized beam has a different optical length than the second vertically polarized beam, it is possible to prevent the two images from overlapping one another. In this way, the two images can be acquired using only one balanced photodetector 71. Thus, the use of the polarized beam distribution unit 30 according to the present embodiment allows a detection unit 70 to be simply implemented with only one balanced photodetector 71.

The polarized beam distribution unit 30 may further include a collimator C. The collimator is disposed at an end of a transmission line from the light distribution unit 20 to the polarization beam splitter 31 to convert light entering the polarization beam splitter 31 into a parallel beam.

In this embodiment, the reference arm 50 may include a linear polarizer 51. The linear polarizer 51 converts light from the light distribution unit 20 into a 45-degree polarized beam containing a horizontal polarization component and a vertical polarization component and emits the 45-degree polarized beam.

The reference arm 50 may further include collimators C disposed at an end of a transmission line from the light distribution unit 20 to the linear polarizer 51 and at an end of a transmission line from the interference unit 60 to the linear polarizer 51, respectively. Accordingly, light entering/exiting the linear polarizer 51 travels in the form of a parallel beam. Here, the 45-degree polarized beam exiting the linear polarizer 51 is transmitted to the interference unit 60.

In this embodiment, the interference unit 60 may include one interferometer 61. As described above, the interferometer 61 may be implemented with a fiber coupler, and one interferometer 61 may include one fiber coupler. Here, the interferometer 61 is connected to the light distribution unit 20 and the reference arm 50. Thus, the interference unit 60 receives the reflected horizontally polarized beam and the reflected vertically polarized beam from the light distribution unit 20 while receiving the 45-degree polarized beam from the reference arm 50 and generates an interference signal of horizontal polarization components by allowing the reflected horizontally polarized beam to interfere with the horizontal polarization component of the 45-degree polarized beam while generating an interference signal of vertical polarization components by allowing the reflected vertically polarized beam to interfere with the vertical polarization component of the 45-degree polarized beam. The two interference signals are transmitted to one balanced photodetector 71 to be converted into electrical signals, as described above.

Figure 6:
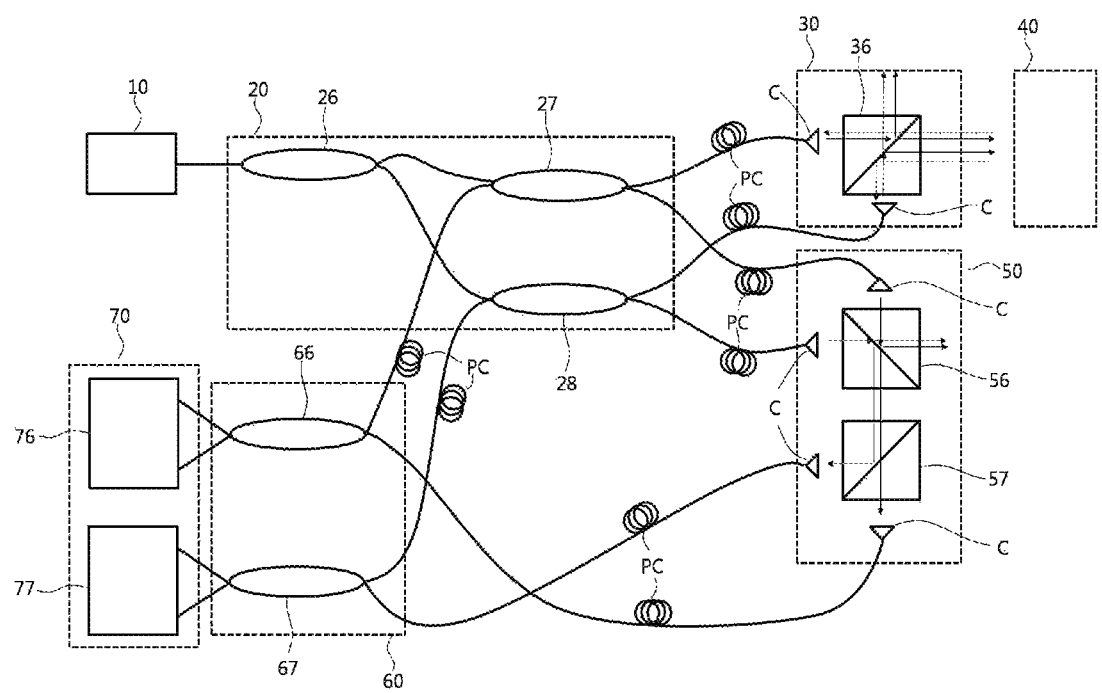
FIG. 6 is a block diagram of a simultaneous orthogonal scanning dual beam OCT system according to a 2-2$^{nd}$ embodiment of the present invention.

Next, a simultaneous orthogonal scanning dual beam OCT system according to a 2-2$^{nd}$ embodiment of the present invention will be described. FIG. 6 is a block diagram of a simultaneous orthogonal scanning dual beam OCT system according to the 2-2$^{nd}$ embodiment of the present invention.

Referring to FIG. 6, a light distribution unit 20 of the simultaneous orthogonal scanning dual beam OCT system according to this embodiment may include a primary beam splitter 26, a first beam splitter 27, and a second beam splitter 28.

The primary beam splitter 26 splits light from a light source 10 into two beams, that is, a first distributed beam and a second distributed beam, and transmits the first distributed beam and the second distributed beam to the first beam splitter 27 and the second beam splitter 28, respectively.

The first beam splitter 27 splits the first distributed beam into two beams and transmits one beam (hereinafter, a "1-1$^{st}$ distributed beam) to a polarized beam distribution unit 30 while transmitting the other beam (hereinafter, a "1-2$^{nd}$ distributed beam") to a reference arm 50. The second beam splitter 28 splits the second distributed beam into two beams and transmits one beam (hereinafter, a "2-1$^{st}$ distributed beam) to the polarized beam distribution unit 30 while transmitting the other beam (hereinafter, a "2-2$^{nd}$ distributed beam") to the reference arm 50.

The first beam splitter 27 receives a reflected horizontally polarized beam from the polarized beam distribution unit 30 described below and transmits the reflected horizontally polarized beam to a first interferometer 66 of an interference unit 60, and the second beam splitter 28 receives a reflected vertically polarized beam from the polarized beam distribution unit 30 and transmits the reflected vertically polarized beam to a second interferometer 67 of the interference unit 60. Here, each of the primary beam splitter 26, the first beam splitter 27, and the second beam splitter 28 may be implemented with a fiber coupler.

Transmission lines may be connected between the light source 10 and the primary beam splitter 26, between the primary beam splitter 26 and each of the first beam splitter 27 and the second beam splitter 28, between the first beam splitter 27 and each of the polarized beam distribution unit 30 and the reference arm 50, between the second beam splitter 28 and each of the polarized beam distribution unit 30 and the reference arm 50, between the first beam splitter 27 and the first interferometer 66, and between the second beam splitter 28 and the second interferometer 67, respectively, wherein each of the transmission lines may be implemented with an optical fiber. Here, a polarization controller (PC) may be disposed on at least one of the transmission lines connected to the first beam splitter 27 or the second beam splitter 28 to maximize intensity of a light beam while allowing the light beam to have a quasi-Gaussian profile.

In this embodiment, the polarized beam distribution unit 30 may include a polarization beam splitter 36, wherein the polarization beam splitter 36 splits a fraction of the first distributed beam, that is, the 1-1$^{st}$ distributed beam into a first horizontally polarized beam and a first vertically polarized beam and transmits the first horizontally polarized beam to the sample arm 40. In addition, the polarization beam splitter 36 splits a fraction of the second distributed beam, that is, the 2-1$^{st}$ distributed beam into a second horizontally polarized beam and a second vertically polarized beam and transmits the second vertically polarized beam to the sample arm 40. Here, light having passed through the sample arm 40 and reflected from the subject S is returned to the polarization beam splitter 36 via the sample arm 40, such that the reflected horizontally polarized beam and the reflected vertically polarized light are transmitted to the first beam splitter 27 and the second beam splitter 28, respectively, via the polarization beam splitter 36.

The polarized beam distribution unit 30 may further include a collimator C. Here, the collimator C may be disposed at an end of each of a transmission line from the first beam splitter 27 to the polarization beam splitter 36 and a transmission line from the second beam splitter 28 to the polarization beam splitter 36 to convert a light beam entering the polarization beam splitter 36 into a parallel beam.

In this embodiment, the reference arm 50 may include a first reference arm polarization beam splitter 56 and a second reference arm polarization beam splitter 57.

The first reference arm polarization beam splitter 56 splits the other fraction of the first distributed beam, that is, the 1-2$^{nd}$ distributed beam into a third horizontally polarized beam and a third vertically polarized beam and transmits the third horizontally polarized beam to the second reference arm polarization beam splitter 57. In addition, the first reference arm polarization beam splitter 56 splits the other fraction of the second distributed beam, that is, the 2-2$^{nd}$ distributed beam into a fourth horizontally polarized beam and a fourth vertically polarized beam and transmits the fourth vertically polarized beam to the second reference arm polarization beam splitter 57.

The second reference arm polarization beam splitter 57 transmits the third horizontally polarized beam and the fourth vertically polarized beam to the first interferometer 66 of the interference unit 60 and the second interferometer 67 of the interference unit 60, respectively.

The reference arm 50 may further include a collimator C. Here, the collimator C may be disposed at an end of at least one of transmission lines from the first beam splitter 27 and the second beam splitter 28 to the first reference arm polarization beam splitter 56 and transmission lines from the first interferometer 66 and the second interferometer 67 to the second reference arm polarization beam splitter 57.

In this embodiment, the interference unit 60 may include the first interferometer 66 and the second interferometer 67.

As described above, the first interferometer 66 receives the reflected horizontally polarized beam and the third horizontally polarized beam from the first beam splitter 27 and the second reference arm polarization beam splitter 57, respectively, and generates an interference signal of vertical polarization components by allowing the reflected horizontally polarized beam to interfere with the third horizontally polarized beam.

As described above, the second interferometer 67 receives the reflected vertically polarized beam and the fourth vertically polarized beam from the second beam splitter 28 and the second reference arm polarization beam splitter 57, respectively, and generates an interference signal of horizontal polarization components by allowing the reflected vertically polarized beam to interfere with the fourth vertically polarized beam.

Each of the first interferometer 66 and the second interferometer 67 may be implemented with a fiber coupler.

The detection unit 70 includes a first balanced photodetector 76 and a second balanced photodetector 77, wherein the first balanced photodetector 76 is connected to the first interferometer 66 to convert the interference signal of horizontal polarization components into an electrical signal and the second balanced photodetector 77 is connected to the second interferometer 67 to convert the interference signal of vertical polarization components into an electrical signal.

Figure 7:
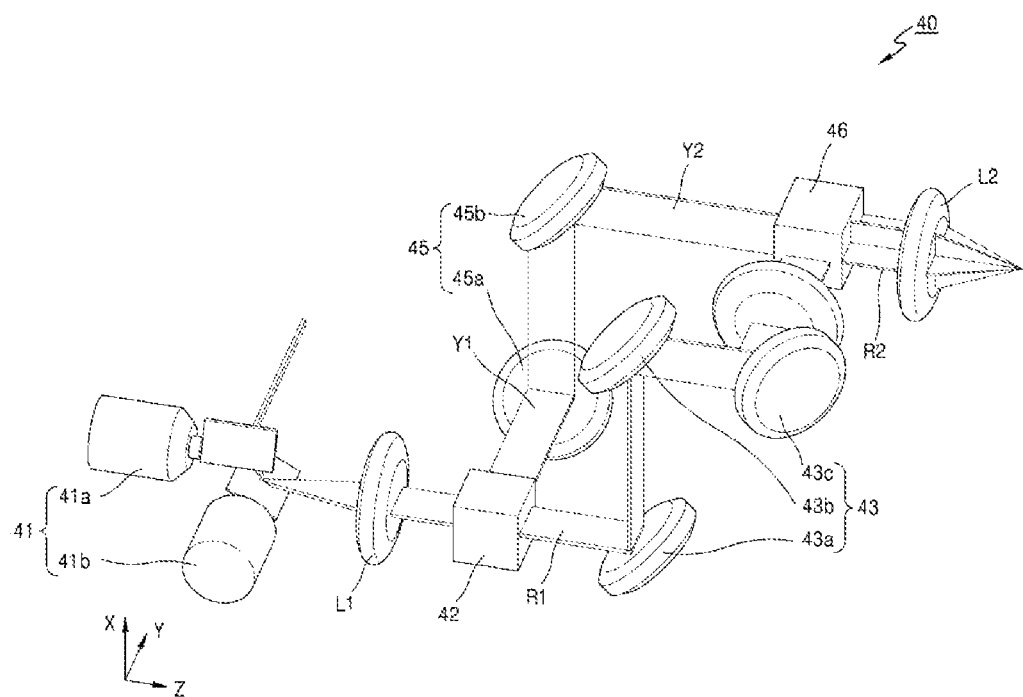
FIGS. 7 and 8 are diagrams of sample arms shown in FIG. 2 to FIG. 6.
Figure 8:
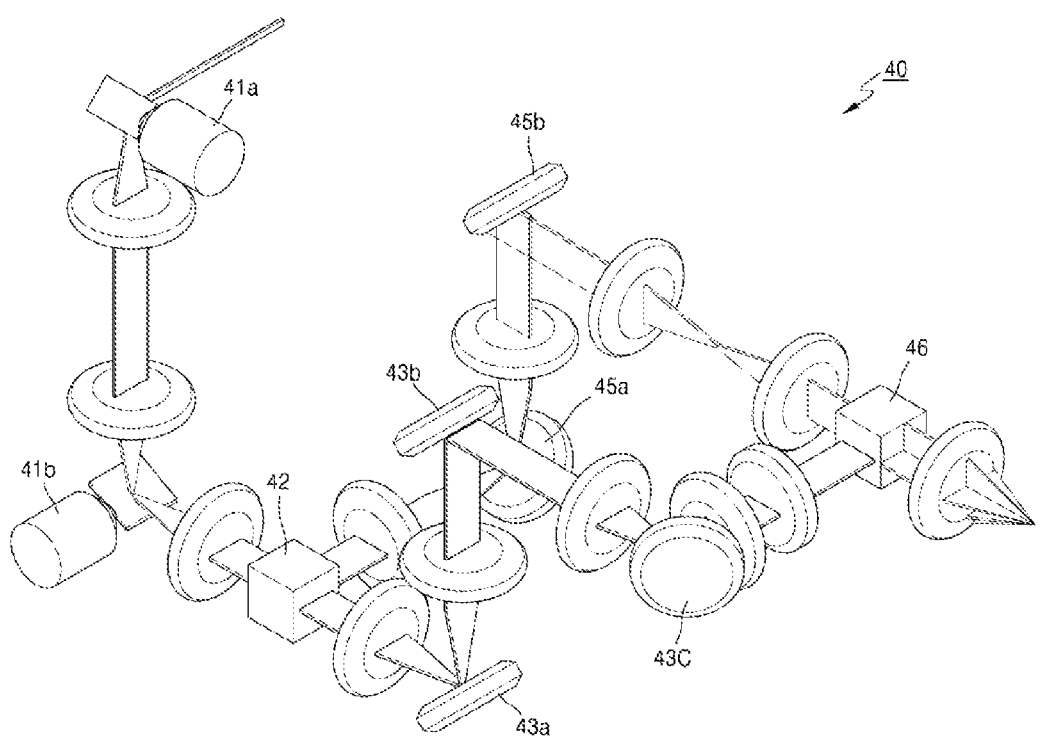

Next, a sample arm 40 of a simultaneous orthogonal scanning dual-beam OCT system according to the present invention will be described in detail. FIGS. 7 and 8 are diagrams of the sample arms shown in FIG. 2 to FIG. 6.

Referring to FIG. 7, the sample arm 40 includes a galvanometer scanner, a first sample arm polarization beam splitter, a first mirror unit, a half-wave plate, a second mirror unit, and a second sample arm polarization beam splitter.

The galvanometer scanner includes a pair of scanning mirrors to scan a subject. Here, the pair of scanning mirrors is rotated about rotational axis located in the X-axis and Z-axis directions in a virtual XYZ three-dimensional space (wherein the X-axis, Y-axis, and Z-axis directions are perpendicular to one another) to reflect incident light in the Z-axis direction.

The first sample arm polarization beam splitter splits light from the galvanometer scanner into a fifth horizontally polarized beam and a fifth vertically polarized beam and allows the fifth horizontally polarized beam to pass in a straight line therethrough and travel in the Z-axis direction while emitting the fifth vertically polarized beam in the X-axis direction, such that the fifth horizontally polarized beam and the fifth vertically polarized beam can travel along different optical paths.

The first mirror unit includes three mirrors 43a, 43b, 43c to define an optical path for the fifth horizontally polarized beam. Here, a 1-1$^{st}$ mirror reflects the fifth horizontally polarized beam in the Y-axis direction, a 1-2$^{nd}$ mirror reflects the fifth horizontally polarized beam from the 1-1$^{st}$ mirror in the Z-axis direction, and a 1-3$^{rd}$ mirror reflects the fifth horizontally polarized beam from the 1-2$^{nd}$ mirror in the X-axis direction. Here, the polarization direction of the fifth horizontally polarized beam having passed through the three mirrors 43a, 43b, 43c is the same as the initial polarization direction of the fifth horizontally polarized beam.

The half-wave plate receives the fifth horizontally polarized beam reflected from the 1-3$^{rd}$ mirror and changes the polarization direction of the fifth horizontally polarized beam by 90 degrees to generate a sixth vertically polarized beam.

The second mirror unit includes two mirrors 45a, 45b to define the optical path and scan direction of the fifth vertically polarized beam emitted from the first sample arm polarization beam splitter. A 2-1$^{st}$ mirror reflects the fifth vertically polarized beam in the Y-axis direction, and a 2-2$^{nd}$ mirror reflects the fifth vertically polarized beam from the 2-1$^{st}$ mirror in the Z-axis direction. When reflected by the 2-2$^{nd}$ mirror, the fifth vertically polarized beam is changed 90 degrees in polarization direction to be converted into a sixth horizontally polarized beam. Here, the scan direction of the sixth horizontally polarized beam corresponds to the X-axis direction.

The second sample arm polarization beam splitter receives the sixth horizontally polarized beam and the sixth vertically polarized beam and simultaneously emits the sixth horizontally polarized beam and the sixth vertically polarized beam in the Z-axis direction in which a subject is placed. Here, the scan direction of the sixth vertically polarized beam corresponds to the Y-axis direction. In this way, the subject can be irradiated with two light beams having perpendicular scan directions, such that one beam scans the subject along the X-axis (fast-axis) at the same time as the other beam scans the subject along the Y-axis (fast-axis).

The sample arm 40 may further include lenses L1, L2. Here, the lens L1 is disposed between the second scanning mirror 41b and the first sample arm polarization beam splitter 42. Since the first scanning mirror 41a is placed at the focal length of the lens L1, a 2D scan image having been scanned by the first scanning mirror 41a and reaching the lens L1 is collimated to form a scan beam.

Figure 1B:
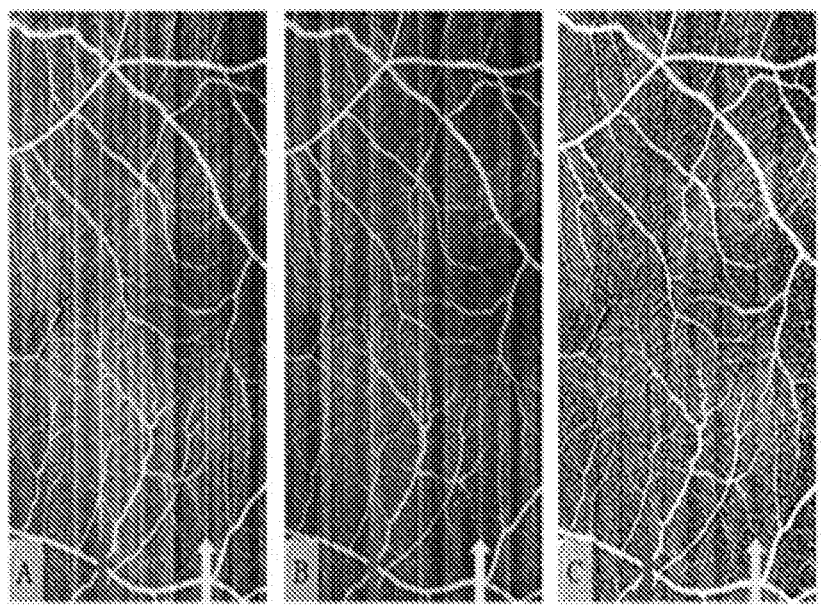

The lens L2 may be disposed to send the sixth horizontally polarized beam and the sixth vertically polarized beam from the second sample arm polarization beam splitter 46 to the same focal region of the subject S (see FIG. 1). When the subject S (see FIG. 1) is the retina, two scan beams are condensed when passing through the cornea and the crystalline lens and are focused on the retina.

Figure 9:
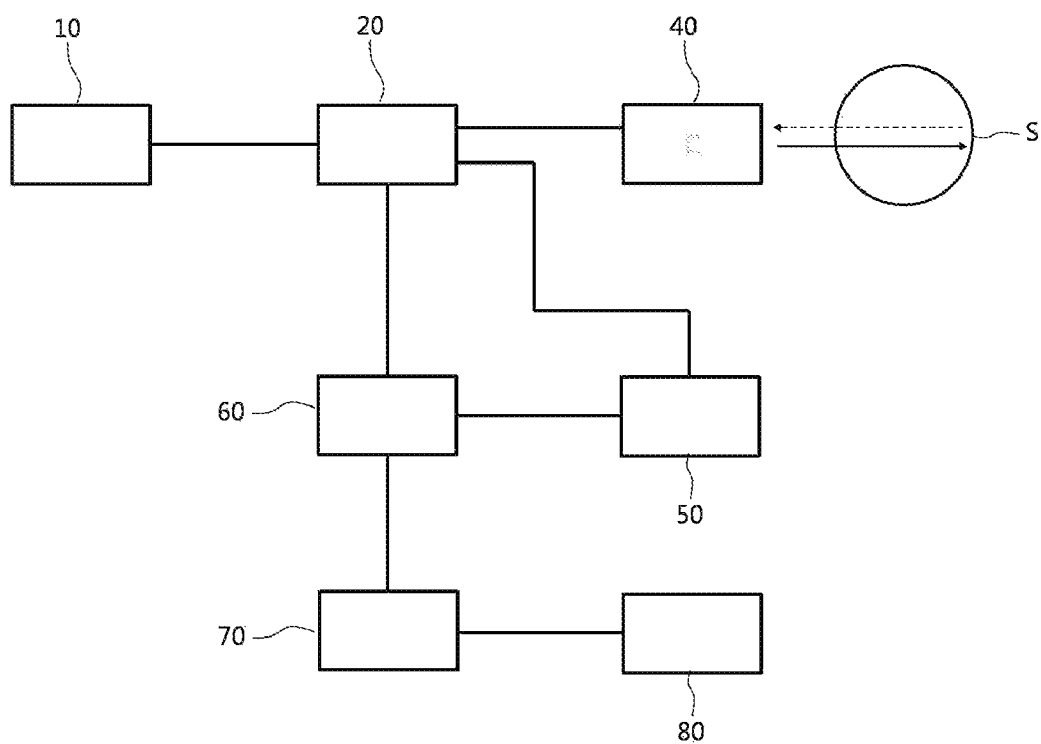
FIG. 9 is a block diagram of a simultaneous orthogonal scanning dual beam OCT system according to a third embodiment of the present invention.
Figure 10:
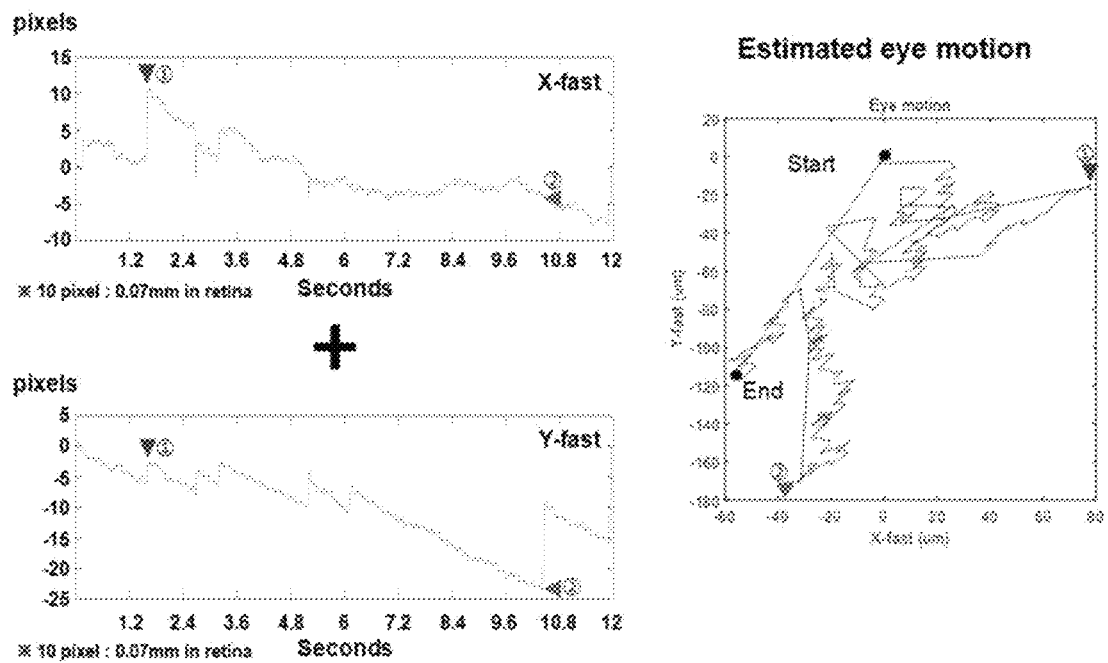
FIG. 10 shows graphs illustrating tracking of eye motion by an image correction unit shown in FIG. 9.

FIG. 9 is a block diagram of a simultaneous orthogonal scanning dual beam OCT system according to a third embodiment of the present invention and FIG. 10 shows graphs illustrating tracking of eye motion by an image correction unit shown in FIG. 9.

Referring to FIG. 9, the simultaneous orthogonal scanning dual beam OCT system according to this embodiment may further include an image correction unit 80.

The image correction unit 80 measures a correlation between an XY plane image and a YZ plane image acquired during scanning to detect motion of a subject and performs image correction based thereon. The image correction unit 80 is implemented with a computing device capable of processing information according to a predetermined algorithm and, first, analyzes a correlation between images acquired during scanning Here, the correlation may be analyzed through time-dependent shift values on images which are acquired through X-fast scan and Y-fast scan, respectively.

Referring to FIG. 10, lateral shift values on the images acquired through X-fast scan and Y-fast scan during scanning of the retina are plotted. In FIG. 10, shift values of 2000 sectional images of the retina acquired for 12 seconds (time for acquisition of one image: 6 ms) are expressed as pixels. Here, 10 pixels correspond to 0.07 mm. Lateral shift values through X-fast scan are shown at the upper left of FIG. 10, lateral shift values through Y-fast scan are shown at the lower left of FIG. 10, and eye motion estimated by integration of the lateral shift values is shown at the right of FIG. 10. At the point indicated by Arrow ① of FIG. 10, large movement appears in the X-fast scan image, whereas only minute movement is observed in the Y-fast scan image. Accordingly, eye motion in the X-axis direction can be detected at that point. At the point indicated by Arrow ②, large movement appears in the Y-fast scan image, whereas only a slight wobble is observed in the X-fast scan image. Accordingly, eye motion in the Y-axis direction can be detected at that point. In this way, the image correction unit 80 detects the motion and shift distance of the subject and compensates for the shift distance due to the eye motion with respect to an image obtained after a point in time at which a great variation in lateral shift value is observed, thereby providing image correction.

Although specific embodiments have been described herein, it should be understood that these embodiments are provided for illustration only and are not to be construed in any way as limiting the present invention, and that various modifications and improvements are possible by those skilled in the art without departing from the spirit and scope of the invention.

Simple modifications and variations of the present invention belong to the scope of the present invention, and the specific scope of the present invention will be clearly defined by the appended claims.

| <List of Reference numerals> | |
| --- | --- |
| S: subject | 10: light source |
| 20: light distribution unit | 30: polarized beam distribution unit |
| 40: sample arm | 50: reference arm |
| 60: interference unit | 70: detection unit |
| 80: image correction unit | |

What is claimed is:

1. A simultaneous orthogonal scanning dual beam optical coherence tomography (OCT) system, comprising:
    a light source generating broadband light;
    a light distribution assembly distributing the light from the light source;
    a sample arm splitting a fraction of the light from the light distribution assembly into a horizontally polarized beam and a vertically polarized beam traveling along different optical paths, simultaneously emitting the horizontally polarized beam and the vertically polarized beam to a subject after converting the horizontally polarized beam and the vertically polarized beam by a sample arm polarization beam splitter such that scanning directions thereof by a galvanometer scanner are perpendicular to one another, and receiving a reflected horizontally polarized beam and a reflected vertically polarized beam from the subject;
    a reference arm splitting the other fraction of the light from the light distribution assembly and generating a reference beam containing a horizontal polarization component and a vertical polarization component by a reference arm polarization beam splitter;
    an interference assembly receiving the reflected horizontally polarized beam, the reflected vertically polarized beam, and the reference beam and generating an interference signal of horizontal polarization components and an interference signal of vertical polarization components allowing simultaneous acquisition of an XZ plane image and a YZ plane image perpendicular to one another; and
    a detection assembly converting the interference signals into electrical signals.

2. The simultaneous orthogonal scanning dual beam OCT system according to claim 1, further comprising:
    a polarized beam distribution assembly splitting a fraction of the light from the light distribution assembly into a horizontally polarized beam and a vertically polarized beam and emitting the horizontally polarized beam and the vertically polarized beam to the sample arm.

3. The simultaneous orthogonal scanning dual beam OCT system according to claim 2, wherein the polarized beam distribution assembly comprises:
    a polarization beam splitter splitting light from the light distribution assembly into a first horizontally polarized beam and a first vertically polarized beam and emitting the first horizontally polarized beam and the first vertically polarized beam;
    a first reflective mirror disposed on a first optical path along which the emitted first vertically polarized beam travels;
    a first quarter-wave plate disposed between the polarization beam splitter and the first reflective mirror to convert the first vertically polarized beam into a second horizontally polarized beam and emit the second horizontally polarized beam to the polarization beam splitter;
    a second reflective mirror disposed on a second optical path along which the emitted first horizontally polarized beam travels; and
    a second quarter-wave plate disposed between the polarization beam splitter and the second reflection mirror to convert the first horizontally polarized beam into a second vertically polarized beam and emit the second vertically polarized beam to the polarization beam splitter, and
    wherein the polarization beam splitter emits the second horizontally polarized beam and the second vertically polarized beam to the sample arm and receives and transmits the reflected horizontally polarized beam and the reflected vertically polarized beam.

4. The simultaneous orthogonal scanning dual beam OCT system according to claim 3, wherein, in the polarized beam distribution assembly, the first reflective mirror is moved along the first optical path or the second reflective mirror is moved along the second optical path such that the second horizontally polarized beam has a different optical length than the second vertically polarized beam.

5. The simultaneous orthogonal scanning dual beam OCT system according to claim 2, wherein the reference arm comprises:

a linear polarizer generating the reference beam by converting light from the light distribution assembly into a 45-degree polarized beam.

6. The simultaneous orthogonal scanning dual beam OCT system according to claim 5, wherein the interference assembly comprises:
one interferometer generating the interference signals by allowing the reflected horizontally polarized beam and the reflected vertically polarized beam to interfere with the reference beam.

7. The simultaneous orthogonal scanning dual beam OCT system according to claim 2, wherein the light distribution assembly comprises:
a primary beam splitter splitting light generated by the light source into a first distributed beam and a second distributed beam;
a first beam splitter transmitting a fraction of the first distributed beam to the polarized beam distribution assembly and transmitting the other fraction of the first distributed beam to the reference arm; and
a second beam splitter transmitting a fraction of the second distributed beam to the polarized beam distribution assembly and transmitting the other fraction of the second distributed beam to the reference arm.

8. The simultaneous orthogonal scanning dual beam OCT system according to claim 7, wherein the polarized beam distribution assembly comprises:
a polarization beam splitter splitting a fraction of the first distributed beam into a first horizontally polarized beam and a first vertically polarized beam and emitting the first horizontally polarized beam to the sample arm, receiving the reflected horizontally polarized beam and transmitting the reflected horizontally polarized beam to the first beam splitter, splitting a fraction of the second distributed beam into a second horizontally polarized beam and a second vertically polarized beam and emitting the second vertically polarized beam to the sample arm, and receiving the reflected vertically polarized beam and transmitting the reflected vertically polarized beam to the second beam splitter.

9. The simultaneous orthogonal scanning dual beam OCT system according to claim 8, wherein the reference arm comprises:
a first reference arm polarization beam splitter splitting the other fraction of the first distributed beam into a third horizontally polarized beam and a third vertically polarized beam, transmitting the third horizontally polarized beam, splitting the other fraction of the second distributed beam into a fourth horizontally polarized beam and a fourth vertically polarized beam, and transmitting the fourth vertically polarized beam; and
a second reference arm polarization beam splitter receiving and separately transmitting the third horizontally polarized beam and the fourth vertically polarized beam.

10. The simultaneous orthogonal scanning dual beam OCT system according to claim 9, wherein the sample arm comprises:
the galvanometer scanner comprising a pair of scanning mirrors rotating about rotational axes located in X-axis and Z-axis directions, respectively, in a virtual XYZ three-dimensional space, the galvanometer scanner sending the received light in the Z-axis direction;
a first sample arm polarization beam splitter splitting the light from the galvanometer scanner into a fifth horizontally polarized beam and a fifth vertically polarized beam and emitting the fifth horizontally polarized beam and the fifth vertically polarized beam in the Z-axis and X-axis directions, respectively;
a first mirror assembly comprising a first Y-axis mirror reflecting the fifth horizontally polarized beam in the Y-axis direction, a first Z-axis mirror reflecting the fifth horizontally polarized beam from the first Y-axis mirror in the Z-axis direction, and a first X-axis mirror reflecting the fifth horizontally polarized beam from the first Z-axis mirror in the X-axis direction;
a half-wave plate converting the fifth horizontally polarized beam from the first X-axis mirror into a sixth vertically polarized beam and emitting the sixth vertically polarized beam;
a second mirror assembly comprising a second Y-axis mirror reflecting the emitted fifth vertically polarized beam in the Y-axis direction and a second Z-axis mirror reflecting the fifth vertically polarized beam from the second Y-axis mirror in the Z-axis direction, the second mirror assembly converting the fifth vertically polarized beam into a sixth horizontally polarized beam; and
a second sample arm polarization beam splitter receiving the sixth horizontally polarized beam and the sixth vertically polarized beam and simultaneously emitting the sixth horizontally polarized beam and the sixth vertically polarized beam in the Z-axis direction, and
wherein the sample arm sends the sixth horizontally polarized beam, a scanning direction of which is the Y-axis direction, and the sixth vertically polarized beam, a scanning direction of which is the X-axis direction, to the subject.

11. The simultaneous orthogonal scanning dual beam OCT system according to claim 1, wherein the interference assembly comprises:
a first interferometer receiving the reflected horizontally polarized beam and the third horizontally polarized beam from the first beam splitter and the second reference arm polarization beam splitter, respectively, and generating the interference signal of horizontal polarization components; and
a second interferometer receiving the reflected vertically polarized beam and the fourth vertically polarized beam from the second beam splitter and the second reference arm polarization beam splitter, respectively, and generating the interference signal of vertical polarization components.

12. The simultaneous orthogonal scanning dual beam OCT system according to claim 11, wherein the detection assembly comprises:
a first balanced photodetector converting the interference signal of horizontal polarization components into an electrical signal; and
a second balanced photodetector converting the interference signal of vertical polarization components into an electrical signal.

13. The simultaneous orthogonal scanning dual beam OCT system according to claim 1, wherein the reference arm comprises:
a polarization beam splitter splitting light from the light distribution assembly into a first horizontally polarized beam and a first vertically polarized beam and emitting the first horizontally polarized beam and the first vertically polarized beam;
a first reflective mirror disposed on a first optical path along which the emitted first vertically polarized beam travels;

a first quarter-wave plate disposed between the polarization beam splitter and the first reflective mirror to convert the first vertically polarized beam into a second horizontally polarized beam and emit the second horizontally polarized beam to the polarization beam splitter;

a second reflective mirror disposed on a second optical path along which the first horizontally polarized beam travels; and a second quarter-wave plate disposed between the polarization beam splitter and the second reflective mirror to convert the first horizontally polarized beam into a second vertically polarized beam and emit the second vertically polarized beam to the polarization beam splitter, and wherein the polarization beam splitter emits the second horizontally polarized beam and the second vertically polarized beam to the interference assembly.

14. The simultaneous orthogonal scanning dual beam OCT system according to claim 1, wherein the sample arm further comprises:

a 4f system comprising a pair of lenses and disposed on at least one of an optical path between the pair of scanning mirrors, an optical path passing through the second sample arm polarization beam splitter, and an optical path between the first sample arm polarization beam splitter and the half-wave plate.

15. The simultaneous orthogonal scanning dual beam OCT system according to claim 1, further comprising:

an image correction assembly measuring a correlation between the images acquired during scanning, detecting motion of the subject, and correcting the images.

* * * * *